United States Patent [19]

Horodysky et al.

[11] 4,253,973
[45] Mar. 3, 1981

[54] PHOSPHORUS-CONTAINING COMPOUNDS AND LUBRICANTS CONTAINING SAME

[75] Inventors: Andrew G. Horodysky, Cherry Hill; Robert M. Gemmill, Jr., Pitman, both of N.J.

[73] Assignee: Mobil Oil Corporation, New York, N.Y.

[21] Appl. No.: 96,115

[22] Filed: Nov. 20, 1979

[51] Int. Cl.$^3$ .............................................. C10M 1/48
[52] U.S. Cl. ............................ 252/46.7; 252/51.5 R; 252/51.5 A; 548/113; 548/216; 548/239
[58] Field of Search ............ 252/32.7 E, 46.7, 51.5 A, 252/51.5 R; 548/113, 216, 239

[56] References Cited

U.S. PATENT DOCUMENTS

| | | | |
|---|---|---|---|
| 2,636,038 | 4/1953 | Branoner | 252/51.5 R X |
| 2,831,858 | 4/1958 | deBenneville et al. | 548/216 X |
| 2,905,644 | 9/1959 | Butter | 252/51.5 R X |
| 2,927,080 | 3/1960 | Westlund, Jr. et al. | 252/46.7 |
| 3,185,647 | 5/1965 | Anderson et al. | 252/46.7 |
| 3,661,922 | 5/1972 | Frump et al. | 548/239 |
| 3,865,740 | 2/1975 | Goldschmidt | 252/46.7 |
| 3,957,746 | 5/1976 | Malec | 252/46.7 |
| 4,028,258 | 6/1977 | Kablaoui et al. | 252/46.7 |
| 4,049,564 | 9/1977 | Ryer et al. | 252/51.5 R X |
| 4,128,558 | 12/1978 | Hendricks et al. | 548/113 X |

*Primary Examiner*—Andrew Metz
*Attorney, Agent, or Firm*—Charles A. Huggett; Michael G. Gilman; Claude E. Setliff

[57] ABSTRACT

Metal salts of phosphosulfurized hydrocarbyl oxazoline phosphorodithioic acids are novel compounds effective for reducing friction and wear when added to a lubricant.

17 Claims, No Drawings

PHOSPHORUS-CONTAINING COMPOUNDS AND LUBRICANTS CONTAINING SAME

BACKGROUND OF THE INVENTION

1. Field of the Invention

The invention is concerned with a novel group of compounds and their use as friction reducing and antiwear additives in lubricants, i.e. lubricant compositions containing same.

2. Discussion of the Prior Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present therein.

Friction is also a problem any time two surfaces are in sliding or rubbing contact. It is of especial significance in an internal combustion engine and related power train components, because loss of a substantial amount of the theoretical mileage possible from a gallon of fuel is traceable directly to friction.

With respect to the novel compounds of this invention, they are made by (1) forming an oxazoline monoester from two moles of monocarboxylic acid and one mole of a hydroxyamine (e.g. 2-amino-2-(hydroxymethyl)-1,3-propanediol), also known as tris(hydroxymethyl)aminomethane, (2) reacting this with phosphorus sulfide and (3) forming a nitrogen-containing compound, an activated olefin derivative or an epoxide derivative. The reaction to prepare the oxazoline monoester, the reaction of the hydroxyl group of the oxazoline with P$_2$S$_5$ and the reaction to form the named derivatives are all well known. However, no art is known that teaches or suggests the novel compounds or their use as lubricant additives.

SUMMARY OF THE INVENTION

In accordance with the invention, there is provided a compound of the formula

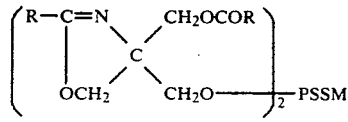

wherein M is derived from a nitrogen-containing compound, an epoxide or an activated olefin and R is a hydrocarbyl group containing from 9 to 49 carbon atoms. The hydrocarbyl group can be alkyl, alkenyl, aryl, aralkyl or alkaryl, wherein the aryl portion contains 6 to 14 carbon atoms.

The invention also provides a lubricant composition comprising the compound as well as a method of reducing fuel consumption in an internal combustion engine.

DESCRIPTION OF SPECIFIC EMBODIMENTS

As has been mentioned hereinabove, the compounds of this invention can be made by reacting a monocarboxylic acid with a hydroxyamine, reacting the product thus formed with a phosphorus sulfide and then with a nitrogen-containing compound, an activated olefin or an epoxide, especially ethylene, propylene or butylene oxide. The following reactions will illustrate synthesis of the novel compounds:

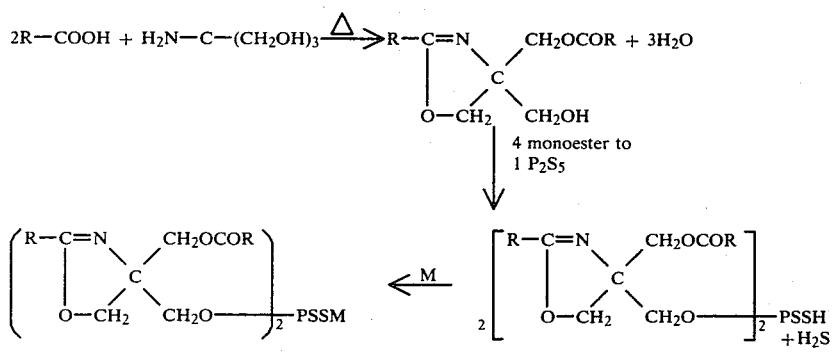

where R and M are as defined above.

The carboxylic acid, as indicated may have from 10 to 50 carbon atoms, including the carboxyl carbon atom. These include the decanoic, dodecanoic, tetradecanoic, octadecanoic, eicosanoic and triacontanoic acids and the like, as well as the unsaturated acid, including particularly oleic acid.

The first reaction, i.e. between the monocarboxylic acid and 2-amino-2-(hydroxymethyl)-1,3-propanediol can be carried out at from about 80° C. to about 250° C., preferably from about 120° C. to about 190° C. The temperature chosen will depend for the most part on the reactants chosen and whether or not a solvent is used. In carrying out this reaction, it is essential that quantities of reactants be chosen such that approximately one hydroxyl remains for the reaction with the phosphorus sulfide. For example, in the reaction illustrated, two moles of the acid and one mole of the amine are required. An excess of acid in this case would lead to the formation of some diester oxazoline in addition to the preferred oxazoline monoester.

In carrying out the reaction to form the phosphorodithioic acid, stoichiometric amounts of the oxazoline and P$_2$S$_5$ are preferred. Generally, however, a slight excess of P$_2$S$_5$, not exceeding about 10 to 20% by weight is preferred. Of course, this will be a matter of choice, the choice being governed by a variety of factors that will be apparent to the art.

The final reaction, i.e. with the nitrogen-containing compound, the activated olefin or epoxide can be carried out at from about 30° C. to about 150° C., preferably from about 70° C. to about 120° C. Again, stoichiometric amounts of reagents are preferred, but if desired, a slight excess can be used. In general, reaction with nitrogen compounds can occur at room temperature to form the amine salt. Reaction with activated olefins and epoxides preferably is carried out by heating to 70°–100° C. for completion to occur in 2–10 hours.

While atmospheric pressure is generally preferred, the reaction can be advantageously run at from about 1 to about 3 atmospheres. Furthermore, where conditions warrant it, a solvent may be used. In general, any relatively non-polar, unreactive solvent can be used, including toluene, xylene and 1,4-dioxane.

The times for the reactions are not critical. Thus, any phase of the process can be carried out in from 1 to 8 hours.

The nitrogen-containing compound used includes a primary, secondary or tertiary straight, branched-chain or cyclic amine containing 10 or more carbon atoms, preferably from 10 to 100 carbon atoms. These further include saturated and unsaturated simple amines, as for example, decyl-, dodecyl- and tridecylamine; tetradecylditetradecyl- and tritetradecylamine; octadecyl-, dioctadecyl- and trioctadecylamine; and the like as well as oleyl amine.

They also include polyalkyleneamines such as the polyalkylene polyamines of the formula NH$_2$(RNH)$_n$RNH$_2$ wherein R may be the same or different and is an alkylene group having from 1 to 5 carbon atoms and n is from 0 to 10. Suitable polyamines may be methylenediamine, ethylenediamine, diethylenetriamine, triethylenetetramine, tetraethylenepentamine, hexaethyleneheptamine and the like. The cyclic amines may be illustrated by mentioning cyclohexylamine and dicyclohexylamine.

The amines may also be aromatic amines wherein the aromatic portion contains 6 to 14 carbon atoms. The activated olefins contemplated include sulfurized olefins and dienes, the dienes having from 10 to 120 carbon atoms. Such compounds also contemplate the use of unsaturated aldehydes of the formula

R'CH=CHCHO unsaturated vinyl esters of the formula

R'CH=CHCOOR"

unsaturated vinylic ethers of the formula

R'CH=CHOR"

unsaturated vinylic ketones of the formula $$R'CH=CH-\overset{O}{\underset{\|}{C}}-R''$$

and acrylonitrile. In these formula, R' and R" may be the same or different hydrocarbyl group, preferably alkyl, and contain from 10 to 100 carbon atoms. R' may also be H.

A further class of compounds that may be employed as reactants are the sulfurized olefins as described in U.S. Pat. No. 3,703,504, the disclosure of which is incorporated herein by reference.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis (p-phenoxy phenyl) ether, phenoxy phenylethers.

It is to be understood, however, that the compositions contemplated herein can also contain other materials. For example, corrosion inhibitors, extreme pressure agents, viscosity index improvers, co-antioxidants, antiwear agents and the like can be used. These materials do not detract from the value of the compositions of this invention, rather the materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions" Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the preformed adducts of the present invention may be employed in any amount which is effective for imparting the desired degree of friction reduction or antiwear activity. In many applications, however, the adduct is effectively employed in amounts from about 0.1% to about 10% by weight, and preferably from about 1 to about 5% of the total weight of the composition.

The following Examples will present illustrations of the invention. They are illustrative only, and are not meant to limit the invention.

EXAMPLE 1

A 12 liter glass reactor fitted with a nitrogen inlet, stirrer, thermometer, Dean-Stark water trap and condenser was used for the reaction.

Oleic acid (20.0 moles, 5649.0 grams), 2-amino-2-(hydroxymethyl)-1,3-propanediol (10.0 moles, 1211.4 grams) and one liter of xylene were charged to the reactor.

The reaction mixture was heated, using a nitrogen purge and rapid stirring, to a maximum temperature of 185° C. for 20 hours. Water evolved over the temperature range of 115°–185° C. A total of 542 ml. of water (theory=540 ml.) was collected. The product was mono(hydroxymethyl)heptadecenyl oxazoline monooleate (hydroxyl no. found 91, calc. 89; mol. wt. found 668, calc. 631).

The mono(hydroxymethyl)heptadecenyl oxazoline monooleate (4.0 moles, 2530.0 grams) (made above) and 500 ml. of toluene were charged to a reactor. $P_2S_5$ (1.20 moles, 268.0 grams) was added slowly over a period of 3.3 hours at a temperature of 48°–96° C. The reaction was run for a total of 13 hours over a temperature range of 48°–96° C. The toluene was removed by vacuum distillation and the product was vacuum filtered through diatomaceous earth filter aid. The final product was a clear, amber, viscous fluid.

EXAMPLE 2

The reaction was performed in a beaker on a hot plate using a magnetic stirrer. The phosphosulfurized product of Example 1 (0.078 mole, 107.6 grams) and oleyl amine (0.078 mole, 20.85 grams) were mixed and heated to 90° C. for 3 hours. The reaction mixture was filtered through diatomaceous earth filter aid. The resulting product was a clear, amber fluid.

EXAMPLE 3

The reaction was performed in a 125 ml. glass reactor fitted with a stirrer, thermometer and condenser. The phosphosulfurized product of Example 1 (0.04 mole, 55.1 grams) and N-oleyl-1,3-propylene diamine (0.02 mole, 6.5 grams) were reacted for 3 hours at 25°–79° C. The reaction product was filtered through diatomaceous earth filter aid. The resulting product was clear, amber fluid.

EXAMPLE 4

Approximately 104 grams of the product of Example 1 was charged to a 250 ml. reactor fitted with a stirrer, thermometer, condenser and addition funnel. The reaction contents were heated to 60° C. and 14 grams of vinyl acetate was added dropwise over a half-hour period. The reactants were then heated to 80°–95° C. for a period of 3 hours. Any unreacted vinyl acetate was removed by vacuum distillation. Approximately, 108 grams of orange liquid was recovered.

EXAMPLE 5

Approximately, 104 grams of the product of Example 1 was charged to a 500 ml. glass reactor fitted with a stirrer, thermometer, condenser and addition funnel. The reactor contents were heated to 85° C. and 10 grams of butyl vinyl ether was added over a period of one hour. The reactants were then agitated at 90°–100° C. for four additional hours. The unreacted butyl vinyl ether was removed by vacuum distillation, leaving a clear orange liquid product.

EXAMPLE 6

Approximately, 104 grams of the product of Example 1 was charged to a 250 ml. reactor equipped with a stirrer, thermometer, condenser, and addition funnel. The reactor contents were heated to 85° C. and 11 grams of ethyl vinyl ether was charged. The reaction mixture was held at 85°–90° C. for an additional three hours. The unreacted ethyl vinyl ether was removed by vacuum distillation to yield a clear orange liquid.

EVALUATION OF THE COMPOUNDS

The compounds were evaluated in a low velocity friction apparatus (LVFA) in a fully formulated 5W-20 synthetic oil containing an additive package including antioxidant, dispersant and detergent. The test compound was 4% of the total weight of oil.

Description

The Low Velocity Friction Apparatus (LVFA) is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured usin a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12-13 ml of test lubricants are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 min. at 250° F., 240 psi, and 40 fpm sliding speed. Afterward, measurements of $U_k$ vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

EVALUATION OF FRICTION REDUCING CHARACTERISTICS

| | Additive Conc. Wt. % in Test Oil | Percent Reduction in Coefficient of Friction at Sliding Speed | |
|---|---|---|---|
| | | 5 Ft./Min. | 30 Ft./Min. |
| Test Oil | 0 | 0 | 0 |
| Example 2 | 4 | 19% | 17% |
| Example 3 | 4 | 25% | 20% |
| Example 4 | 4 | 14% | 11% |
| Example 5 | 4 | 6% | 4% |
| Example 6 | 4 | 12% | 17% |

Representative samples of the above prepared compositions were also tested for copper corrosivity using ASTM No. D130-9 at 210° F. for six hours. Table 2 summarizes the results obtained.

TABLE 2

COPPER STRIP CORROSIVITY

| | Concentration in 200" SPN[2] | Copper Corrosivity Rating |
|---|---|---|
| Example 3 | 1 | 1B |
| | 3 | 1B |
| Example 4 | 1 | 2B |
| | 3 | 2B |
| Example 5 | 1 | 2A |
| | 3 | 2A |

[2]200 second solvent paraffinic neutral mineral oil.

Representative samples of the above prepared compositions were further evaluated for antioxidant properties with a catalytic oxidation test. A sample of the base lubricant was placed in an oven at 325° F. Present in the sample were the following metals either known to catalyze organic oxidation or commonly used materials of construction:

a. 15.6 sq. in. of sand-blasted iron wire
b. 0.78 sq. in. of polished copper wire
c. 0.87 sq. in. of polished aluminum wire
d. 0.167 sq. in. of polished lead surface.

Dry air was passed through the sample at a rate of about 5 liters per hour for 40 hours. Table 3 shows the data obtained:

TABLE 3

Catalytic Oxidation Test 325° F., 40 Hours

| | Conc. Wt. % | Percent Incr. in Visc. of Oxidized Oil, KV @ 100° C. | Neutralization Number |
|---|---|---|---|
| Base Oil 200" Solvent Paraffinic Neutral Lubricating Oil | 0 | 27 | 2.21 |
| Example 3 | 1 | 9 | 1.85 |
| | 3 | 6 | 1.86 |

We claim:

1. A compound of the formula

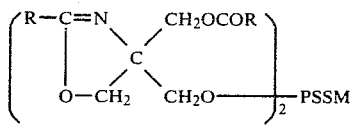

wherein M is the residue of a nitrogen-containing compound selected from the group consisting of (1) primary, secondary and tertiary amines containing 10 or more carbon atoms and (2) a polyalkyleneamine, an epoxide or an activated olefin selected from the group consisting of dienes, unsaturated aldehydes, vinylic esters, vinylic ethers, vinylic ketones, acrylonitrile and sulfurized olefins and R is a hydrocarbyl group containing from 9 to 49 carbon atoms.

2. The compound of claim 1 wherein R is a heptadecenyl group.

3. The compound of claim 1 wherein the polyalkyleneamine is a polyalkyleneamine of the formula

wherein R is an alkylene group having 1 to 5 carbon atoms and n is from 1 to 10.

4. The compound of claim 1 wherein the nitrogen-containing compound is oleyl amine.

5. The compound of claim 1 wherein the nitrogen-containing compound is N-oleyl-1,3-propylene diamine.

6. The compound of claim 1 wherein the activated olefin is vinyl acetate.

7. The compound of claim 1 wherein the activated olefin is ethyl vinyl ether.

8. The compound of claim 1 wherein the activated olefin is butyl vinyl ether.

9. A lubricant composition comprising a major proportion of a lubricant and a friction reducing or antiwear amount of a compound of the formula

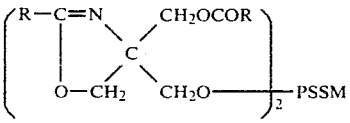

wherein M is the residue of a nitrogen-containing compound selected from the group consisting of (1) primary, secondary and tertiary amines containing 10 or more carbon atoms and (2) a polyalkyleneamine, an epoxide or an activated olefin selected from the group consisting of dienes, unsaturated aldehydes, vinylic esters, vinylic ethers, vinylic ketones, acrylonitrile and sulfurized olefins and R is a hydrocarbyl group containing from 9 to 49 carbon atoms.

10. The composition of claim 9 wherein R is a heptadecenyl group.

11. The composition of claim 9 wherein the polyalkyleneamine is a polyalkyleneamine of the formula NH$_2$(RNH)$_n$RNH$_2$ wherein R is an alkylene group having 1 to 5 carbon atoms and n is from 1 to 10.

12. The composition of claim 9 wherein the nitrogen-containing compound is oleyl amine.

13. The composition of claim 9 wherein the nitrogen-containing compound is N-oleyl-1,3-propylene diamine.

14. The composition of claim 9 wherein the activated olefin in vinyl acetate.

15. The composition of claim 9 wherein the activated olefin is ethyl vinyl ether.

16. The composition of claim 9 wherein the activated olefin is butyl vinyl ether.

17. A method of reducing the fuel consumption of an internal combustion engine by lubricating said engine with a lubricating oil composition comprising a major proportion of a lubricating oil and a friction reducing amount of a compound of the formula

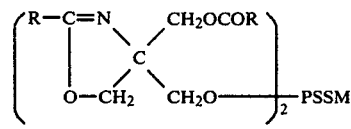

wherein M is the residue of a nitrogen-containing compound selected from the group consisting of (1) primary, secondary and tertiary amines containing 10 or more carbon atoms and (2) a polyalkyleneamine, an epoxide or an activated olefin selected from the group consisting of dienes, unsaturated aldehydes, vinylic esters, vinylic ethers, vinylic ketones, acrylonitrile and sulfurized olefins and R is a hydrocarbyl group containing from 9 to 49 carbon atoms.

* * * * *

UNITED STATES PATENT AND TRADEMARK OFFICE
CERTIFICATE OF CORRECTION

PATENT NO. : 4,253,973
DATED : March 3, 1981
INVENTOR(S) : Andrew G. Horodysky and Robert M. Gemmill, Jr.

It is certified that error appears in the above-identified patent and that said Letters Patent are hereby corrected as shown below:

Column 3, line 52, the formula " R'CH=CHOR" " should read -- R'CH=CHOR' --.

Signed and Sealed this

Sixteenth Day of June 1981

[SEAL]

Attest:

RENE D. TEGTMEYER

*Attesting Officer*  *Acting Commissioner of Patents and Trademarks*